(12) United States Patent
Zimmermann et al.

(10) Patent No.: US 7,528,290 B2
(45) Date of Patent: May 5, 2009

(54) APPARATUSES AND METHODS FOR SEPARATING BUTENE-1 FROM A MIXED $C_4$ FEED

(75) Inventors: Joseph E. Zimmermann, Arlington Heights, IL (US); Dennis E. O'Brien, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 343 days.

(21) Appl. No.: 11/617,069

(22) Filed: Dec. 28, 2006

(65) Prior Publication Data

US 2008/0161618 A1 Jul. 3, 2008

(51) Int. Cl.
*C07C 7/00* (2006.01)
*B01D 3/14* (2006.01)

(52) U.S. Cl. ............... 585/809; 585/314; 585/324; 585/258; 202/152; 202/153; 202/155; 202/158; 202/161; 202/163; 202/168; 202/169; 202/170

(58) Field of Classification Search ............ 585/809, 585/314, 324, 258; 202/152, 153, 155, 158, 202/161, 163, 169, 170
See application file for complete search history.

(56) References Cited

U.S. PATENT DOCUMENTS

| | | | | |
|---|---|---|---|---|
| 4,797,133 | A | * | 1/1989 | Pujado ............ 44/449 |
| 5,709,780 | A | * | 1/1998 | Ognisty et al. ...... 202/158 |
| 5,755,933 | A | | 5/1998 | Ognisty et al. |
| 6,156,947 | A | | 12/2000 | Vora |
| 6,166,279 | A | | 12/2000 | Schwab et al. |
| 6,175,049 | B1 | | 1/2001 | Stuwe et al. |
| 6,264,799 | B1 | | 7/2001 | Stuwe et al. |
| 6,271,430 | B2 | | 8/2001 | Schwab et al. |
| 6,433,240 | B1 | | 8/2002 | Schwab et al. |
| 6,461,574 | B2 | | 10/2002 | Korhonen et al. |
| 6,468,399 | B2 | | 10/2002 | Stuwe et al. |
| 6,538,168 | B1 | | 3/2003 | Schwab et al. |
| 6,551,465 | B1 | | 4/2003 | Van Zile et al. |
| 6,552,242 | B1 | | 4/2003 | Rice |
| 6,558,515 | B1 | * | 5/2003 | Steacy ............ 203/1 |
| 6,580,009 | B2 | | 6/2003 | Schwab et al. |

(Continued)

OTHER PUBLICATIONS

Schultz et al., "Reduce Costs with Dividing-Wall Columns", CEP, pp. 64-71 (May 2002).*

(Continued)

*Primary Examiner*—Walter D Griffin
*Assistant Examiner*—Huy-Tram Nguyen
(74) *Attorney, Agent, or Firm*—James C. Paschall

(57) ABSTRACT

A process is disclosed for recovering 1-butene from a feed steam comprising n-butane, isobutane and butene isomers using a single, divided wall distillation column. The disclosed process includes introducing the feed steam into an inlet of a first side of a distillation column, wherein the distillation column comprises a top, a bottom and a center dividing wall extending between the bottom and the top of the column and dividing the column into the first side and a second side. The process includes taking off an isobutane stream from the top of the second side of column, taking off a 1-butene stream as a bottoms stream from the second side of the column, and taking off a combination 2-butene and n-butane stream as a bottom stream from the first side of column.

20 Claims, 3 Drawing Sheets

U.S. PATENT DOCUMENTS

| | | |
|---|---|---|
| 6,645,350 B1 | 11/2003 | Steacy |
| 6,646,172 B1 | 11/2003 | Schwab et al. |
| 6,846,389 B2 | 1/2005 | Kaibel et al. |
| 6,887,434 B2 | 5/2005 | Schwab et al. |
| 7,001,490 B2 * | 2/2006 | Wostbrock et al. ............. 203/1 |
| 7,118,653 B2 | 10/2006 | Brady et al. |
| 7,132,038 B2 | 11/2006 | Bohner et al. |
| 2001/0003140 A1 | 6/2001 | Schwab et al. |
| 2002/0002317 A1 | 1/2002 | Schwab et al. |
| 2002/0197190 A1 | 12/2002 | Schwab et al. |
| 2003/0106786 A1 * | 6/2003 | Kaibel et al. ................. 203/74 |
| 2003/0181772 A1 * | 9/2003 | Meyer et al. ................ 585/324 |
| 2004/0011706 A1 * | 1/2004 | Kaibel et al. ................ 208/347 |
| 2004/0181111 A1 | 9/2004 | Sigl et al. |
| 2006/0021911 A1 * | 2/2006 | Adrian et al. ............... 208/115 |
| 2006/0157336 A1 * | 7/2006 | Kaibel et al. ................... 203/1 |
| 2006/0161010 A1 | 7/2006 | Gobbel et al. |

OTHER PUBLICATIONS

Maralikrishna et al., "Development of Dividing Wall Distillation Column Design space for a specified separation", Institution of Chemical Engineers Trans IChemE, vol. 80, Part A, pp. 155-166 (Mar. 2002).*

* cited by examiner

APPARATUSES AND METHODS FOR SEPARATING BUTENE-1 FROM A MIXED $C_4$ FEED

BACKGROUND

1. Technical Field

Apparatuses and processes for the recovery of 1-butene from a mixed $C_4$ feed stream are disclosed. More specifically, this disclosure is directed toward methods and apparatuses for the separation of 1-butene from a mixed $C_4$ feed of 1-butene, 2-butene, isobutane and n-butane, using a single distillation column.

2. Description of the Related Art

Olefinic hydrocarbons are feedstocks for a variety of commercially important reactions that yield fuels, polymers, oxygenates and other chemical products. In the industrially important OXO process, olefins react catalytically with carbon monoxide and hydrogen to give aldehydes. Olefins are polymerized by heating with catalysts to give high-octane gasolines, plastics, and synthetic rubber.

The specific isomer, the position of the double bond and the degree of branching of an olefin all may be important to the efficiency of a chemical reaction or to the properties of the final product. Thus, it is often desirable to isomerize olefins to increase the output of the desired isomer. Further, because the distribution of isomers in a mixture of olefins is rarely optimum for a specific application, the separation of isomers is an important industrial process.

One group of olefins, butenes (also known as butylenes, $C_4H_8$), serve as intermediates in the preparation of a variety of organic compounds. Butenes are formed during the catalytic cracking of petroleum to produce gasoline. Butenes can also be prepared commercially by the catalytic dehydrogenation of butanes. Butenes include four isomeric compounds belonging to the series of olefinic hydrocarbons: 1-butene; cis-2-butene; trans-2-butene; and isobutene. All four butene isomers are gases at room temperature and pressure.

Butenes are among the most useful olefins having more than one isomer. Butenes are utilized for the production of octanes, which are traditional components of gasoline. Butenes are converted to octanes by reacting butenes with isobutane or by dimerizing two butenes to form octenes, which, upon hydrogenation, yield octanes. On treatment with water in the presence of catalysts, butenes are transformed into secondary and tertiary butyl alcohols, which are used as commercial solvents.

Secondary-butyl alcohol and methylethyl ketone, as well as butadiene, are important derivatives of 2-butenes. The most important derivative influencing isobutene and 2-butene isomer demand may be methyl t-butyl ether (MTBE) which is an important component of gasoline. Isobutene also finds application in such products as methyl methacrylate, polyisobutene and butyl rubber.

Demand for 1-butene has been growing rapidly based on its use as a co-monomer for linear low-density polyethylene and as a monomer in polybutene production 1-butene is also used in the manufacture of other polyethylenes, polypropylenes, polybutenes, butylene oxides and the $C_4$ solvents secondary butyl alcohol (SBA) and methyl ethyl ketone (MEK). The co-polymerisation of ethylene and 1-butene produces a form of polyethylene that is more flexible and more resilient. 1-butene can also help to create a more versatile range of polypropylene resins.

The isolation of 1-butene from mixed feed of butane and the other butane isomers currently requires at least two distillation processes as best seen in FIG. 1. In the described process, the first distillation performed in the column 10, a mixed $C_4$ feed enters the column 10 through the line 11. 1-butene and isobutane are separated from butane and the 2-butenes of the mixed $C_4$ feed. Specifically, 1-butene and isobutane leave the column from the overhead line 12, pass through the condenser 13/collector 13' and are fed to the next column 14 through the line 15. Part of the at least partially condensed isobutane/1-butene stream is recycled back to the column 10 through the line 16 and control valve 17. A mixture of n-butane and 2-butene exits the column 10 through the bottoms outlet line 18 which is connected to a product line 19 and a recycle line 21. Part of the butane/2-butene stream passes through the recycle line 21 and heat exchanger 22 where it is reboiled prior to reentering the column 10 as shown.

In the second distillation, carried out in column 14, the isobutane and 1-butene are separated. Specifically, the isobutene/1-butene feed enters the column 14 through the line 15 and isobutane exits the column 14 through the overhead outlet line 23, passes through the condenser 24/collector 24' before proceeding on to the outlet line 25. Part of the isobutane overhead product is recycled through the line 26 and control valve 27. The 1-butene leaves the column 14 through the bottoms outlet 28 and product outlet line 29 as controlled by the control valve 31. Part of the bottoms outlet 28 is recycled through the heat exchanger or boiler 32 before re-entering the column 14.

Because of the increasing demand for 1-butene, there is a need for a more efficient process for separating 1-butene from the other butene isomers, isobutane and n-butane

SUMMARY OF THE DISCLOSURE

In satisfaction of the aforenoted needs, a process for recovering 1-butene from a feed stream comprising n-butane, isobutane and butene isomers is disclosed. The disclosed process comprises: introducing the feed steam into an inlet of an distillation column, the distillation column comprising a top, a bottom and a center vertical dividing wall extending from the bottom to the top of the column, the dividing wall dividing the column into a first side and a second side, the inlet being disposed on the first side; taking off an isobutane stream from the top of the second side of the column; taking off a 1-butene stream as a bottoms stream from the second side of the column; and taking off a combination 2-butene and n-butane stream as a bottoms stream from the first side of the column.

In a refinement, the feed stream comprises n-butane, isobutane, 1-butene and 2-butene.

In another refinement, the feed stream comprises less than 10 vol % isobutene. In a related refinement, the feed stream has been withdrawn from a reaction process that the removes isobutene.

In another refinement the feed stream comprises less than 10 vol % butadiene. In a related refinement the feed stream has been withdrawn from a reaction process that the removes butadiene.

In another refinement the first side of the column is connected to a first side overhead stream, and the process further comprises introducing at least a portion of the first side overhead stream to the second side of the column as a second feed.

In a related refinement, the process further comprises condensing at least a portion of the first side overhead stream and returning the at least partially condensed portion to the first side of the column as reflux.

In another refinement, all of the first side over head stream is introduced to the second side of the column as the second feed, and the process further comprises condensing the isobutane stream and introducing at least a portion of the 1-butene stream and at least a portion of the isobutane stream to the first side of the column as reflux.

In a refinement, the dividing wall comprises an internal passageway extending downward and providing fluid communication between a top area of the first side of the column to a receiving area disposed in a mid-section of the second side of the column, and the process further comprises introducing overhead vapor from the top area of the first side of the column as feed to the receiving area of the second side of the column.

Another process for recovering 1-butene from a feed stream comprising n-butane, isobutane, 1-butene and 2-butene is disclosed, wherein the feed stream does not contain substantial amounts of isobutene or butadiene. This disclosed process comprises: introducing the feed steam into a first side of a distillation column, the distillation column further comprising a top, a bottom and a center dividing wall extending from the top to the bottom and dividing the column into a first side and a second side, the first side comprising an overhead area and a bottoms area, the second side comprising an overhead area and a bottoms area; taking off an isobutane stream from the overhead area of the second side of the column; taking off a 1-butene stream from the bottoms area of the second side of the column; taking off a combination 2-butene and n-butane stream from the bottoms area of the first side of the column; and introducing at least partially condensed overhead vapor from the first side of the column as a second feed stream to the second side of the column.

In a refinement, the process further comprises condensing at least a portion of the overhead vapor from the first side of the column and returning the at least partially condensed portion to the first side of the column as reflux.

In a refinement, the process further comprises condensing the isobutane stream and introducing at least a portion of the 1-butene stream and at least a portion of the at least partially condensed isobutane stream to the first side of the column as reflux.

In a refinement, the dividing wall comprises an internal passageway extending downward and providing fluid communication between a top area of the first side of the column to a receiving area disposed in a mid-section of the second side of the column, and the process further comprises condensing overhead vapor from the top area of the first side of the column in the internal passageway and communicating the at least partially condensed overhead vapor as the second feed to the receiving area of the second side of the column.

Yet another process is disclosed for recovering 1-butene from a feed stream comprising n-butane, isobutane, 1-butene and 2-butene, wherein the feed stream does not contain substantial amounts of isobutene or butadiene. This process comprises: introducing the feed steam into a first side of a distillation column, the distillation column further comprising a top, a bottom and a center dividing wall extending from the top to the bottom and dividing the column into a first side and a second side, the first side of the column being isolated from the second side of the column, the first side comprising an overhead area and a bottoms area, the second side comprising an overhead area and a bottoms area; taking off an isobutane stream from the overhead area of the second side of the column and condensing the isobutane stream; taking off a 1-butene stream from the bottoms area of the second side of the column; taking off a combination 2-butene and n-butane stream from the bottoms area of the first side of the column; introducing at least partially condensed overhead vapor from the first side of the column as a second feed stream to the second side of the column; and introducing at least a portion of the at least partially condensed isobutane stream and at least a portion of the 1-butene stream to the overhead area of the first side of the column as reflux.

A dividing wall fractional distillation column is disclosed for recovering 1-butene from a feed stream comprising n-butane, isobutane, 1-butene and 2-butene, wherein the feed stream does not contain substantial amounts of isobutene or butadiene. The distillation column comprises: an outer vessel enclosing an internal cylindrical volume and comprising a top and a bottom; a dividing wall extending vertically through the vessel and dividing the vessel into adjacent the first and second sides, the first side comprising an overhead area and a bottoms area, the second side comprising an overhead area and a bottoms area; the first side comprising a first feed inlet for introducing the feed stream into the first side of the vessel, a first bottoms outlet for removing a 2-butene/butane stream from the bottoms area of the first side of the vessel, and the overhead area of the first side of the vessel be in communication with a second feed inlet disposed in the second side of the vessel; the second side comprising the second feed inlet for introducing overhead vapor from the first side of the vessel to the second side of the vessel, a second bottoms outlet for removing 1-butene from the bottoms area of the second side of the vessel and a second side overhead outlet for removing an isobutane stream from the overhead area of the second side of the vessel In a refinement, the dividing wall comprises an internal passageway providing communication between the overhead area of the first side of the vessel and the second feed inlet of the second side of the vessel.

Thus, 1-butene can be separated from the feed stream comprising n-butane, isobutane and 2-butene using a single process contained within a single distillation column. The disclosed process and make advantageous use of a strategically placed dividing wall within the column. Thus, by employing a single column as opposed to dual columns, both capital construction and operating costs are reduced.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are illustrated schematically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein and that numerous variations will be apparent to those skilled in the art.

DETAILED DESCRIPTION OF THE PRESENTLY PREFERRED EMBODIMENTS

Fractionation columns, also referred to as distillation columns, find many applications in various industrial processes. A conventional fractionation column is typically employed to separate an entering feed stream into two fractions. These are referred to as the overhead and bottoms fraction, with the overhead fraction being the lighter or more volatile components of the feedstream. The feedstream may comprise only two components which are separated into high purity streams within the fractionation column. In this instance the overhead stream and the bottoms stream would each be rich in one of the two components of the feedstream. In many instances, however, the feedstream contains three or more compounds. These mixtures are typically divided by boiling point range into fractions which may each contain numerous different volatile compounds.

Figure 1:
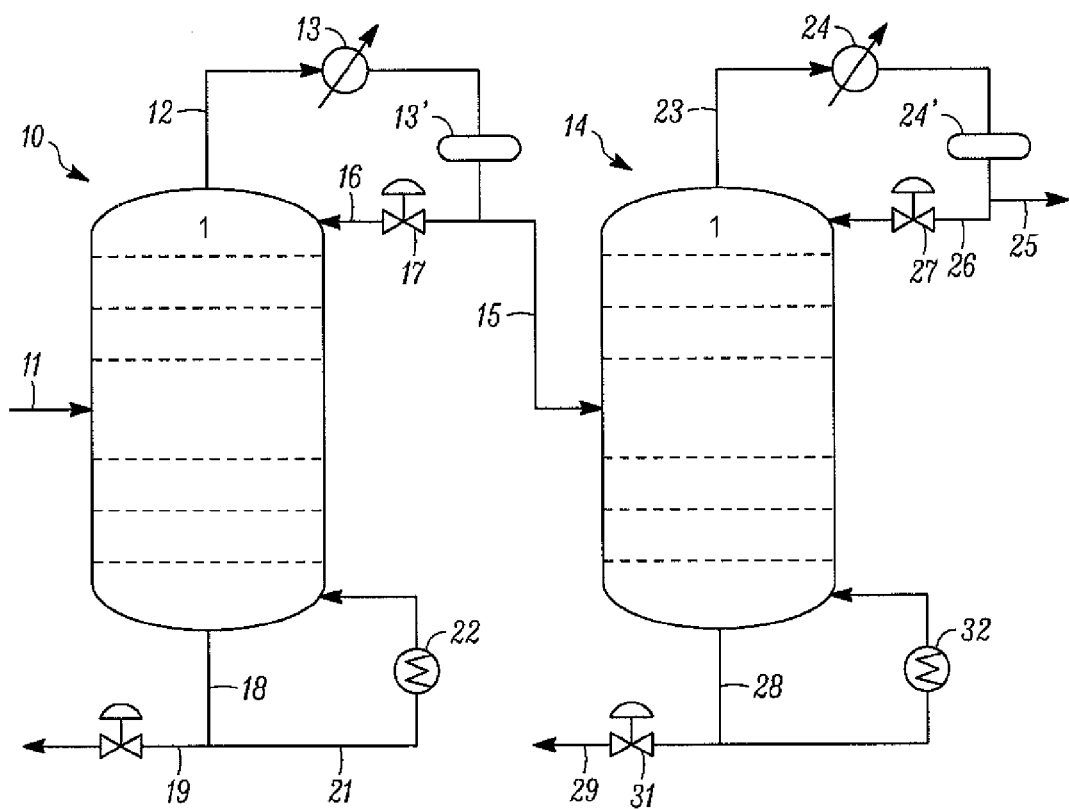
FIG. 1 is a schematic illustration of a prior art 1-butene separation process from a mixed $C_4$ feed requiring two distillation columns or distillation processes.

In order to separate a feedstream comprising four compounds into single product streams, each rich in one of the, compounds with conventional columns it has been necessary to employ two such fractionation columns. As illustrated in FIG. 1, the first fractionation column 10 would form an overhead product stream 12 having a high content of the lighter component, in this case 1-butene and isobutane, and a second bottoms product stream 18 containing the heavier components, in this case n-butane and 2-butene. As seen in FIG. 1, the overhead product stream 12 is then passed into the second fractionation column 14 to divide the overhead product into two other product streams, the isobutane stream 25 and the 1-butene stream 28

Disclosed herein is a novel strategy for the separation of 1-butene from a mixed $C_4$ feed that includes isobutane, n-butane, 2-butene and 1-butene. The novel strategy disclosed herein is the employment of a "dividing wall" fractionation column which lowers the capital and operating costs in comparison to the construction and operation of two separate fractionation columns as illustrated in FIG. 1.

Figure 2:
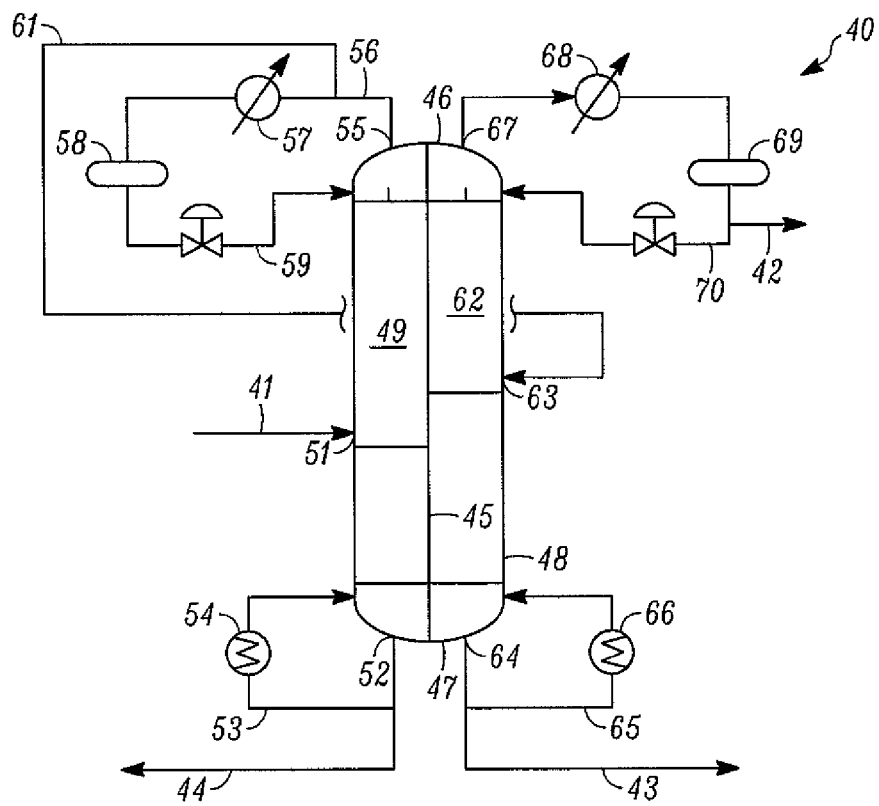
FIG. 2 is a schematic illustration of a disclosed process for separating 1-butene from a mixed $C_4$ feed using a single distillation column equipped with a dividing wall and wherein reflux from the first half of the column is used as a feed for the second half of the column.

Referring now to FIG. 2, a dividing wall column 40 is disclosed which separates a $C_4$ mixed feed 41 that includes 1-butene, 2-butene, isobutane and n-butane into an overhead stream 42 consisting primarily of isobutane, one bottoms outlet stream 43 consisting primarily of 1-butene and another bottoms outlet stream 44 consisting essentially of n-butane and 2-butene. The overhead stream 42 of isobutane and the bottom stream 43 of 1-butene are both disposed opposite the dividing wall 45 from the feed stream 41 and the bottoms stream 44 of n-butane and 2-butene.

The dividing wall 45 extends from a top 46 and to a bottom end 47 of the vessel 48. In the first, left half or feed half 49, the feed 41 enters at a feed inlet 51. The higher boiling point materials, 2-butene and n-butane, migrate downward towards the bottoms outlet 52 which is in communication with the bottoms outlet line 44. Part of the bottom stream 44 is recycled though the line 53 and reboiler 54 Vapors extend upwardly through the left side 49 of the column 40 and towards the overhead outlet 55 and overhead line 56. Part of the flow from the overhead line 56 passes through a condenser 57 and receiver 58 before reentering the column 40 as reflux through the line 59. Another portion of the overhead stream 56 is carried through the return line 61 to the right side 62 of the column 40 were it re-enters through a second feed inlet 63. The return stream 61 includes primarily isobutane and 1-butene as the n-butane and 2-butene leave the left side 49 column 40 through the bottoms line 44.

In the right side 62 of the column 40, the higher boiling 1-butene migrates down toward the bottoms outlet 64 which is in communication with the 1-butene outlet stream 43. Part of the bottoms flow is recycled through the line 65 which passes through the heat exchanger 66 before reentering the column 40. At the top 46 of the column 40, an overhead line 42 is connected to an overhead outlet 67. The net overhead line 42 is the isobutane outlet stream and passes through the condenser 68 and receiver 69. Part of the isobutane overhead is returned to the column 40 as reflux through the line 70

Thus, in FIG. 2 (and in FIGS. 3-4 for that matter), the first separation takes place in the left side 49 of the column 40 where n-butane and 2-butene is separated from isobutane and 1-butene. In the right side 62 of the column 40, isobutane is separated from 1-butene. The reader will note that the column 40 of FIG. 2 uses two condensers, one for each overhead stream disposed on its side of the dividing wall 45, while the embodiments described below in connection with FIGS. 3-4 reduce the condenser count by at least one.

Figure 3:
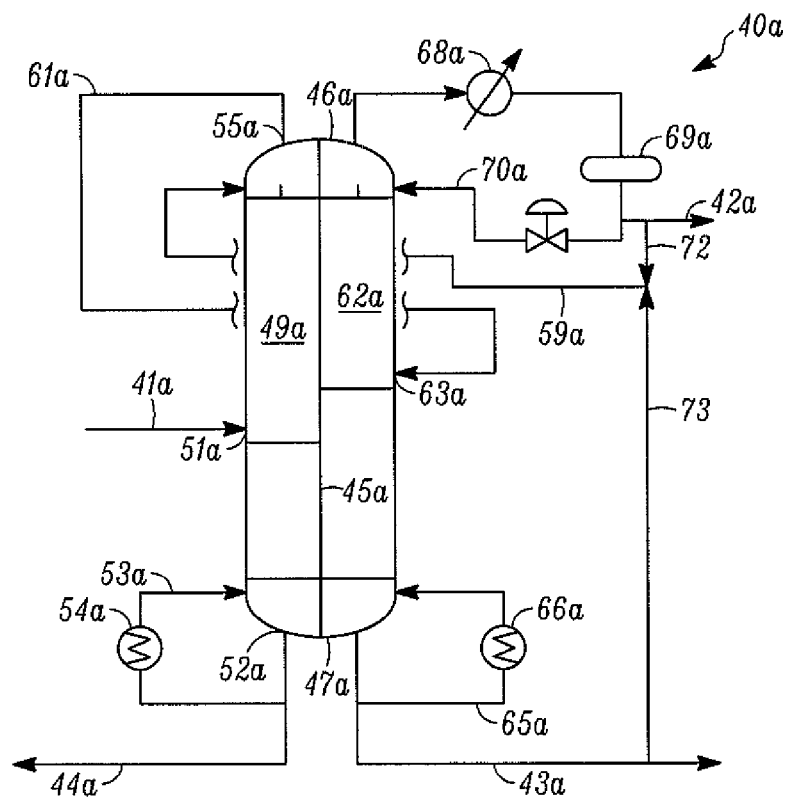
FIG. 3 is a schematic illustration of another disclosed process for separating 1-butene from a mixed $C_4$ feed also using a single distillation column equipped with a dividing wall and wherein the reflux from the first half of the column is also used as the feed for the second half of the column but also wherein the reflux also includes portions of the isobutene and 1-butane product streams thereby eliminating the need for a condenser and receiver for the overhead of the first half of the column.

Specifically, turning to FIG. 3, using the same reference numerals used for FIG. 2 for identical components but with the suffix "a," the column 40a does not require a condenser for the reflux line 59a as the reflux line 59a is taken off the isobutane outlet line 42a and at the 1-butene line 43a through the lines 72, 73 respectively thereby taking advantage of the fact that the isobutane in the line 42a has passed through the condenser 68a and receiver 69a and the 1-butene in the line 43a is already condensed liquid. Therefore, the reflux line 59a comprises at least partially condensed isobutane and 1-butene and therefore a separate condenser is not required this reflux line 59a. In reflux line 70a provides at least partially condensed reflux flow to the right side 62a of the column 40a.

Figure 4:
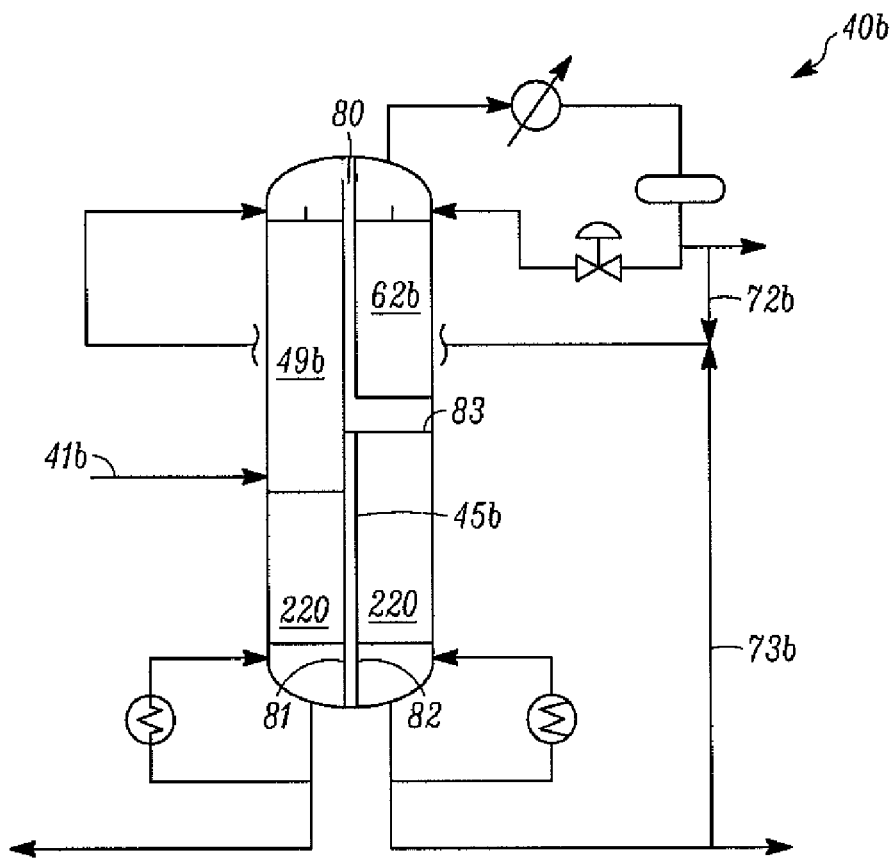
FIG. 4 is a schematic illustration of yet another disclosed process for separating 1-butene from a mixed $C_4$ feed using a single distillation column equipped with a dividing wall and wherein the reflux from the first half of the column is also used as the feed for the second half of the column but the reflux is fed to the second half of the column through a double dividing wall with a vapor feed inlet to the second half of the column.

Turning to FIG. 4, using the same reference numerals used for FIGS. 2-3 for identical components but with the suffix "b," an embodiment similar to the column 40a of FIG. 3 is disclosed but the column 40b of FIG. 4 includes a divided wall 45b that has a central passageway 80 disposed between two opposing walls 81, 82. The central passageway 80 enables reflux and overhead vapors from the left side 49b of the column 40b to migrate downward through the passageway 80 and into the receiving area 83 in the left side 62b of the column 40b. Thus, the column 40b does not include an exterior line such as that shown at 61, 61a in FIGS. 2-3 for the purpose of transmitting left side 49, 49a overhead to the right side 62, 62a of the column. Instead, the interior dividing wall 45b provides communication between the left side 49b overhead and the right side 62b receiving area 83 in the form of the passageway 80. As shown, the passageway 80 extends down to the receiving tray 83. The wall 82 extends to the bottom 47b for to allow column modification in the future and to move the feed tray 83 with a minimal amount of work.

Figure 5:
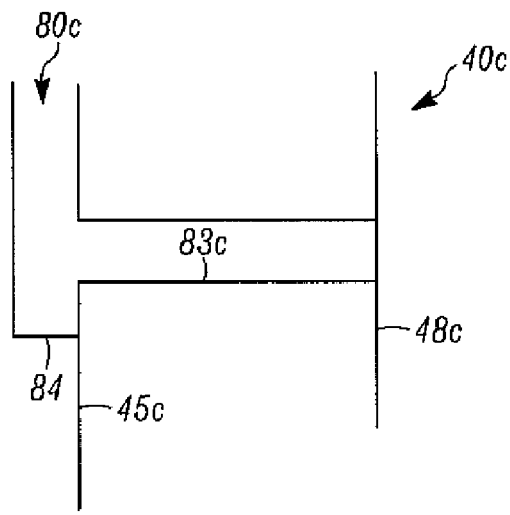
FIG. 5 is an enlarged view of the area of a variation on the feed inlet through the dividing wall as illustrated in FIG. 4.

In FIG. 5, an alternative design is employed where the wall 82 does not extend along the entire wall 81, but terminates at the end wall 84 disposed below the receiving tray 83*c*.

In an embodiment, a fractionation column 40 may be characterized as a dividing wall fractional distillation column which comprises an outer vessel 48 comprising a enclosing an internal cylindrical volume, the outer vessel 48 being aligned in a vertical direction when in use, a dividing wall 45 extending vertically through the internal cylindrical volume and dividing the cylindrical volume into first side 49 and second adjacent side 62, an inlet 51 for feeding a process stream 41 into the first side 49 of the column 40, a reflux flow from the first side 49 of the column 40 serving as a feed for the second side 62 of the column 40, the first side 49 having a bottoms stream 44 for removing heavies, the second side 62 having outlet overhead stream 42 for removing light product and a bottoms stream 43 for removing heavy product.

While only certain embodiments have been set forth, alternatives and modifications will be apparent from the above description to those skilled in the art. These and other alternatives are considered equivalents and within the spirit and scope of this disclosure and the appended claims.

What is claimed:

1. A process for recovering 1-butene from a feed stream comprising n-butane, isobutane and butene isomers, the process comprising:
   introducing the feed steam into an inlet of an distillation column, the distillation column comprising a top, a bottom and a center vertical dividing wall extending from the bottom to the top of the column, the dividing wall dividing the column into a first side and a second side, the inlet being disposed on the first side;
   taking off an isobutane stream from the top of the second side of the column;
   taking off a 1-butene stream as a bottoms stream from the second side of the column; and
   taking off a combination 2-butene and n-butane stream as a bottoms stream from the first side of the column.

2. The process of claim 1 wherein the feed stream comprises n-butane, isobutane, 1-butene and 2-butene.

3. The process of claim 1 wherein the feed stream comprises less than 10 vol % isobutene.

4. The process of claim 1 wherein the feed stream has been withdrawn from a reaction process that the removes isobutene.

5. The process of claim 1 wherein the feed stream comprises less than 10 vol % butadiene.

6. The process of claim 1 wherein the feed stream has been withdrawn from a reaction process that the removes butadiene.

7. The process of claim 1 wherein the first side of the column is connected to a first side overhead stream, and
   the process further comprises introducing at least a portion of the first side overhead stream to the second side of the column as a second feed.

8. The process of claim 7 wherein the process further comprises condensing at least a portion of the first side overhead stream and returning the at least partially condensed portion to the first side of the column as reflux.

9. The process of claim 7 wherein all of the first side overhead stream is introduced to the second side of the column as the second feed, and
   the process further comprises condensing the isobutane stream and introducing at least a portion of the 1-butene stream and at least a portion of the isobutane stream to the first side of the column as reflux.

10. The process of claim 1 wherein the dividing wall comprises an internal passageway extending downward and providing fluid communication between a top area of the first side of the column to a receiving area disposed in a mid-section of the second side of the column, and
    the process further comprises introducing overhead vapor from the top area of the first side of the column as feed to the receiving area of the second side of the column.

11. A process for recovering 1-butene from a feed stream comprising n-butane, isobutane, 1-butene and 2-butene, wherein the feed stream does not contain substantial amounts of isobutene or butadiene, the process comprising:
    introducing the feed steam into a first side of a distillation column, the distillation column further comprising a top, a bottom and a center dividing wall extending from the top to the bottom and dividing the column into a first side and a second side, the first side comprising an overhead area and a bottoms area, the second side comprising an overhead area and a bottoms area;
    taking off an isobutane stream from the overhead area of the second side of the column;
    taking off a 1-butene stream from the bottoms area of the second side of the column;
    taking off a combination 2-butene and n-butane stream from the bottoms area of the first side of the column; and
    introducing at least partially condensed overhead vapor from the first side of the column as a second feed stream to the second side of the column.

12. The process of claim 11 wherein the process further comprises condensing at least a portion of the overhead vapor from the first side of the column and returning the at least partially condensed portion to the first side of the column as reflux.

13. The process of claim 11 wherein the process further comprises condensing the isobutane stream and introducing at least a portion of the 1-butene stream and at least a portion of the at least partially condensed isobutane stream to the first side of the column as reflux.

14. The process of claim 11 wherein the dividing wall comprises an internal passageway extending downward and providing fluid communication between a top area of the first side of the column to a receiving area disposed in a mid-section of the second side of the column, and
    the process further comprises condensing overhead vapor from the top area of the first side of the column in the internal passageway and communicating the at least partially condensed overhead vapor as the second feed to the receiving area of the second side of the column.

15. A process for recovering 1-butene from a feed stream comprising n-butane, isobutane, 1-butene and 2-butene, wherein the feed stream does not contain substantial amounts of isobutene or butadiene, the process comprising:
    introducing the feed steam into a first side of a distillation column, the distillation column further comprising a top, a bottom and a center dividing wall extending from the top to the bottom and dividing the column into a first side and a second side, the first side of the column being isolated from the second side of the column, the first side comprising an overhead area and a bottoms area, the second side comprising an overhead area and a bottoms area,
    taking off an isobutane stream from the overhead area of the second side of the column and condensing the isobutane stream;

taking off a 1-butene stream from the bottoms area of the second side of the column;

taking off a combination 2-butene and n-butane stream from the bottoms area of the first side of the column;

introducing at least partially condensed overhead vapor from the first side of the column as a second feed stream to the second side of the column; and introducing at least a portion of the at least partially condensed overhead from the second side of the column and at least a portion of the 1-butene stream to the overhead area of the first side of the column as reflux.

16. The process of claim 15 wherein the process further comprises condensing at least a portion of the first side overhead vapor and returning the at least partially condensed portion to the first side of the column as reflux.

17. The process of claim 15 wherein the process further comprises condensing the isobutane stream and introducing at least a portion of the 1-butene stream and at least a portion of the at least partially condensed isobutane stream to the first side of the column as reflux.

18. The process of claim 15 wherein the dividing wall comprises an internal passageway extending downward and providing fluid communication between a top area of the first side of the column to a receiving area disposed in a mid-section of the second side of the column, and the process further comprises the overhead vapor as the second feed to the receiving area of the second side of the column.

19. A dividing wall fractional distillation column for recovering 1-butene from a feed stream comprising n-butane, isobutane, 1-butene and 2-butene, wherein the feed stream does not contain substantial amounts of isobutene or butadiene, comprising:

an outer vessel enclosing an internal cylindrical volume and comprising a top and a bottom;

a dividing wall extending vertically through the vessel and dividing the vessel into adjacent the first and second sides, the first side comprising an overhead area and a bottoms area, the second side comprising an overhead area and a bottoms area;

the first side comprising a first feed inlet for introducing the feed stream into the first side of the vessel, a first bottoms outlet for removing a 2-butene/butane stream from the bottoms area of the first side of the vessel, and the overhead area of the first side of the vessel being in communication with a second feed inlet disposed in the second side of the vessel;

the second side comprising the second feed inlet for introducing overhead vapor from the first side of the vessel to the second side of the vessel, a second bottoms outlet for removing 1-butene from the bottoms area of the second side of the vessel and a second side overhead outlet for removing an isobutane stream from the overhead area of the second side of the vessel.

20. The distillation column of claim 19 wherein the dividing wall comprises an internal passageway providing communication between the overhead area of the first side of the vessel and the second feed inlet of the second side of the vessel.

* * * * *